(12) United States Patent
Godbole

(10) Patent No.: US 6,793,776 B2
(45) Date of Patent: Sep. 21, 2004

(54) OPERATION OF HEADS COLUMN

(75) Inventor: Sanjay P. Godbole, Solon, OH (US)

(73) Assignee: The Standard Oil Company, Warrenville, IL (US)

( * ) Notice: Subject to any disclaimer, the term of this patent is extended or adjusted under 35 U.S.C. 154(b) by 0 days.

(21) Appl. No.: 09/945,228

(22) Filed: Aug. 31, 2001

(65) Prior Publication Data

US 2002/0029952 A1 Mar. 14, 2002

Related U.S. Application Data

(63) Continuation of application No. 09/227,665, filed on Jan. 8, 1999, now Pat. No. 6,296,739.

(51) Int. Cl.[7] .......................... B01D 3/42; C07C 255/08; C01C 3/06
(52) U.S. Cl. ...................... 203/6; 203/99; 203/DIG. 19; 203/100; 558/463; 558/468; 423/372
(58) Field of Search ................... 203/2, 6, 99, DIG. 19, 203/100, 75, 78; 558/463, 466, 303; 423/372

(56) References Cited

U.S. PATENT DOCUMENTS 3,885,928 A * 5/1975 Wu .............................. 55/854
4,234,510 A * 11/1980 Wu ............................ 558/466
5,959,134 A * 9/1999 Keckler et al. ............. 558/320
6,054,603 A * 4/2000 Godbole .................... 558/466

FOREIGN PATENT DOCUMENTS

| EP | 0024788 | 3/1981 |
| EP | 0053518 A | 6/1982 |
| FR | 1588427 A | 4/1970 |
| GB | 2041372 A | 9/1980 |

OTHER PUBLICATIONS

Database CA "Online" ChemicalAbstracts Service, Columbus, Ohio,Database Accession No. 72:124810/DN Abstract, M. Kurabayashi, K. Yanagiya, M. Yasumoto; vol. 71, No. 8, 1968, pp. 1119–1123.

* cited by examiner

Primary Examiner—Virginia Manoharan
(74) Attorney, Agent, or Firm—Thomas E. Nemo

(57) ABSTRACT

A process for the enhanced recovery and operation of hydrogen cyanide (HCN)/heads column obtained from the reactor effluent of an ammoxidation reaction of propane, propylene or isobutylene by reducing the polymer formation above the feed tray in the heads tower.

9 Claims, 1 Drawing Sheet

OPERATION OF HEADS COLUMN

This application is a con of Ser. No. 09/227,665 Jan. 8, 1999 now U.S. Pat. No. 6,296,739.

SUMMARY

The present invention is directed to an improved process for the manufacture of acrylonitrile or methacrylonitrile. In particular, the present invention is directed to improved operation of the heads, or HCN separation, column in the acrylonitrile and methacrylonitrile recovery process. Applicant has discovered a previously unknown relationship between the formation of undesirable polymeric HCN in the heads column and the formation of an aqueous second liquid phase in the heads column above the feed tray. The present invention is directed towards preventing the formation of the aqueous phase in the heads column above the feed tray, since the presence of this aqueous phase causes the formation of unwanted and detrimental polymeric HCN. Previous art was directed at reducing the pressure of the heads tower, resulting in lower operating temperatures and perceived reduction in the polymerization rates of HCN. The instant invention is directed at disrupting the mechanism of the HCN polymerization, which occurs as ionic polymerization in the aqueous phase. By practicing the present invention, unwanted polymerization of HCN may be reduced, fouling of the heads column may be greatly diminished or eliminated, and increased production of desirable products may be achieved.

FIELD OF THE INVENTION

The present invention is directed to an improved process for the manufacture of acrylonitrile or methacrylonitrile. In particular, the present invention is directed to the improvement in the recovery and operation of hydrogen cyanide separation column utilized during the manufacture of acrylonitrile or methacrylonitrile.

Recovery of acrylonitrile/methacrylonitrile produced by the ammoxidation of propane, propylene or isobutylene on a commercial scale has been accomplished by quenching the reactor effluent with water followed by passing the gaseous stream containing acrylonitrile or methacrylonitrile, as well as byproduct HCN, resulting from the quench to an absorber where water and the gases are contacted in counter-current flow to remove substantially all the acrylonitrile or methacrylonitrile. The aqueous stream containing HCN and the acrylonitrile or methacrylonitrile is then passed through a series of distillation columns and associated decanters for separation and purification of product acrylonitrile or methacrylonitrile from a vapor stream containing substantially all the HCN.

Typical recovery and purification systems that are used during the manufacture of acrylonitrile or methacrylonitrile are disclosed in U.S. Pat. Nos. 4,234,510 and 3,885,928, assigned to the assignee of the present invention and herein incorporated by reference.

SUMMARY OF THE INVENTION

It is the primary object of the present invention to provide an improved process for the recovery and operation of byproduct HCN in the manufacture of acrylonitrile or methacrylonitrile.

Another object of the present invention is to provide an improved process for the recovery of acrylonitrile, methacrylonitrile, or HCN obtained from the reactor effluent of an ammoxidation reaction of propane, propylene or isobutylene comprising passing the reactor effluent through an absorber column, a recovery column and a heads column wherein the improvement comprises operating the heads column in a manner which inhibits the formation of an aqueous phase above the feed tray of the heads column.

An additional object of the present invention is to provide an improved process for the recovery of acrylonitrile, methacrylonitrile, or HCN obtained from the reactor effluent of an ammoxidation reaction of propane, propylene or isobutylene by operating the heads column in a manner which inhibits the formation of an aqueous phase above the feed tray of the heads column, such as increasing reflux ratios; using a side decanter to split and remove the aqueous phase from the column; using a cooler feed stream to increase the stripping in the column; increasing the number of stripping trays; using an intermediate condenser above the feed to supplement the overhead condenser; subcooling the reflux stream; increasing reboiler and overhead condenser duties to increase reflux flow rates; control operating pressure to shift the equilibrium between the two liquid phases; and other methods known to those skilled in the art that would increase reboiler duty, and the associated stripping effectiveness of the heads column. Increasing the hydrogen cyanide reflux or concentration of hydrogen cyanide above the feed tray can also be achieved through higher HCN production levels for eliminating the second liquid phase. Any increased tray efficiency also allows more stripping effectiveness and is helpful in eliminating the undesired second liquid phase.

Yet another object of the present invention is to provide an improved process for the recovery of acrylonitrile, methacrylonitrile, or HCN obtained from the reactor effluent of an ammoxidation reaction of propane, propylene or isobutylene comprising passing the reactor effluent through an absorber column, a recovery column and a heads column wherein the improvement comprises feeding extra HCN to the heads column, either by operating the ammoxidation reactor in a manner to produce a higher concentration of HCN to other products, or by recycling HCN to the heads column, to permit operation of the heads column in a manner that reduces or eliminates the formation of the undesirable aqueous phase.

Additional objects, advantages and novel features of the invention will be set forth in part in the description which follows, and in part, will become apparent to those skilled in the art upon examination of the following or may be learned by the practice of the invention. The objects and advantages of the invention may be realized and obtained by means of the instrumentalities and combinations particularly pointed out in the appended claims. To achieve the foregoing and other objects and in accordance with the purpose of the present invention as embodied and broadly described herein, the process of the present invention comprises transporting the reactor effluent obtained during the ammoxidation of propane, propylene or isobutylene to a quench column wherein the hot effluent gases are cooled by contact with an aqueous spray, passing the cooled reactor effluent overhead to an absorber column wherein the HCN and crude acrylonitrile or methacrylonitrile is absorbed in water, passing the aqueous solution containing the HCN and acrylonitrile or methacrylonitrile, plus other impurities to a first distillation column (recovery column), where a significant portion of the water and impurities are removed as a liquid bottoms product, while HCN, water, a minor portion of impurities and acrylonitrile or methacrylonitrile are remove as an overhead vapor stream. This overhead vapor stream is further cooled using a heat exchanger, and directed to a decanter, to separate and condense liquids which are returned to the recovery process, while the remaining vapor stream is directed to a flare, incinerator, or other disposal process. The organic stream is fed to the heads column for separation of HCN from acrylonitrile.

In a preferred embodiment of the present invention, the process is performed with the reactor effluent obtained from the ammoxidation of propane or propylene, ammonia and oxygen to produce acrylonitrile.

In a still preferred embodiment of the present invention, the reactor effluent is obtained by the reaction of propane, propylene, ammonia and air in a fluid bed reactor while in contact with a fluid bed catalyst. Conventional fluid bed ammoxidation catalyst may be utilized in the practice of the invention. For example, fluid bed catalyst as described in U.S. Pat. Nos. 3,642,930 and 5,093,299, herein incorporated by reference, may be utilized in the practice of the present invention.

DETAILED DESCRIPTION OF THE INVENTION

Figure 1:
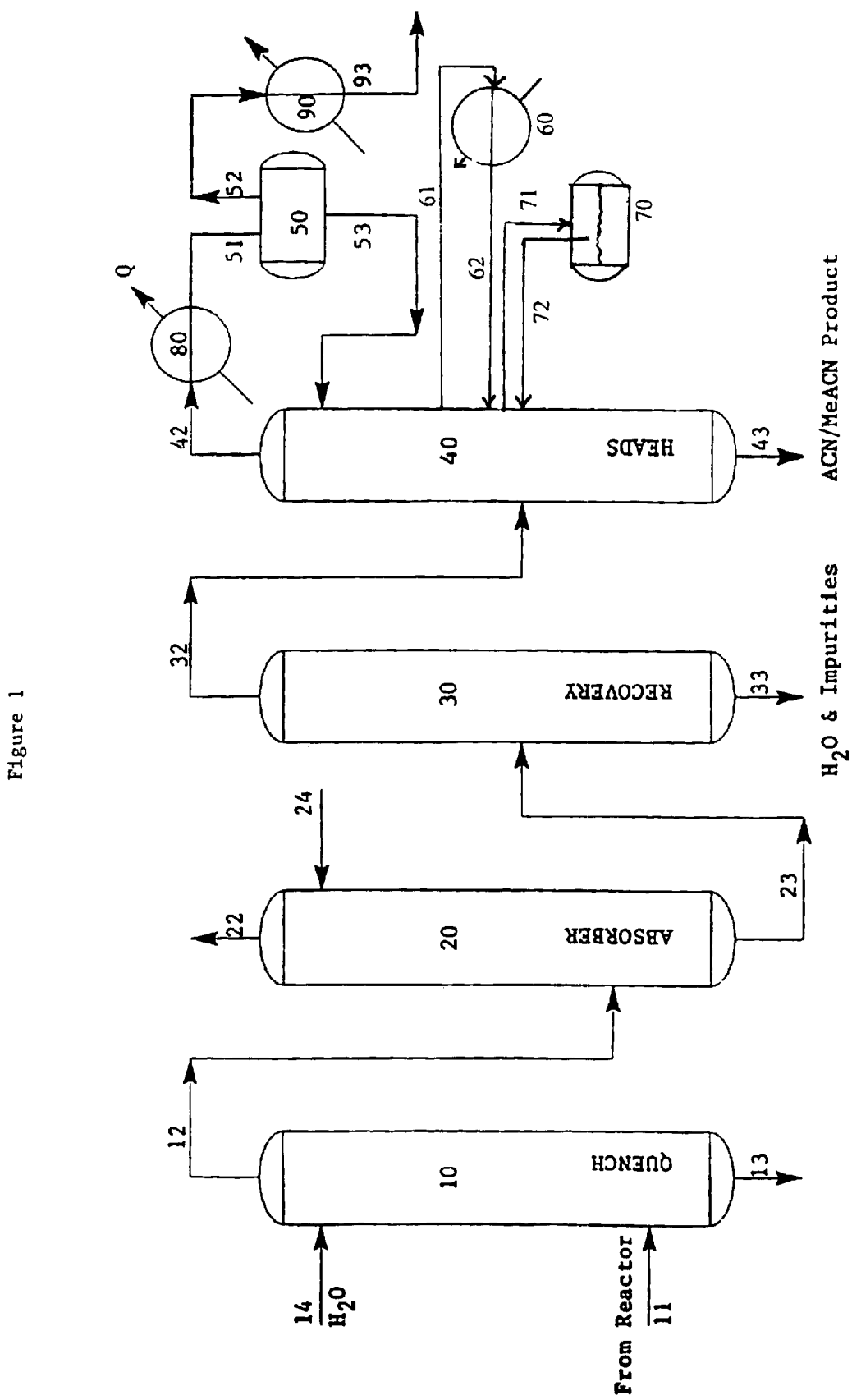
FIG. 1 is a schematic representation of the process as it applies to the manufacture of acrylonitrile and improved recovery and operation of HCN separation column.

The general recovery and purification of acrylonitrile of methacrylonitrile, and the present invention will now be described in detail with reference to FIG. 1. The reactor effluent 11 obtained by the ammoxidation of propane, propylene or isobutylene, ammonia and oxygen containing gas in a fluid bed reactor (not shown) while in contact with a fluid bed ammoxidation catalyst is transported to a quench column 10 via transfer line 11, wherein the hot effluent gases are cooled by contact with water spray 14. The cooled effluent gas containing the desired product (acrylonitrile or methacrylonitrile, acetonitrile and HCN) is then passed into the bottom of an absorber column 20 via line 12 wherein the products are absorbed in water which enters absorber column 20 from the top via line 24. The non-absorbed gases pass from the absorber through pipe 22 located at the top of the absorber 20. The aqueous stream containing the desired product is then passed via line 23 from the bottom of absorber 20 to the upper portion of a first distillation column 30 (recovery column) for further product purification. The product is recovered from the top portion of recovery column 30 and sent to a second distillation column 40 (heads column) 40 via line 32, while water and other impurities are removed from the recovery column 30 via line 33. In the heads column 40, the HCN is taken overhead and removed from the column via line 42, cooled in overhead condenser 80, and the resulting material directed to reflux drum 50 via line 51. Liquid reflux from the reflux drum 50 is returned to the upper portion of the heads tower via line 53. Vapor phase material is removed from the reflux drum 50 via line 52 and cooled in HCN product condenser 90. Optional intermediate condenser 60 can be added to heads column 40. Material is withdrawn from column 40 above feedline 32 by line 61, cooled, and returned to the heads column 40 by line 62. Optional decanter 70 can be added to heads column 40. Side material is withdrawn from column 40 by line 71 and the organic phase is returned by line 72.

A significant operational problem experienced in the recovery and purification of products in the acrylonitrile and methacrylonitrile production process is the formation of polymeric HCN in the heads column, sometimes also known as the HCN column (40). In particular, polymeric HCN forms on the trays and internals in the heads column above the column feed location (where line 32 enters column 40). The solid, polymeric HCN fouls distillation trays, over flow weirs, downcomers, and the like, as well as disrupting the hydraulic balance of the liquid/vapor interfaces in the heads column. The polymerization increases the column pressure drop, and the corresponding increased temperatures in the column further increases the polymer formation. This polymer eventually requires a costly and time consuming shutdown of the purification section and a column cleaning exercise.

A less precise understanding of the phenomena led prior practitioners to reduce the operating pressure and hence temperature of the heads column, thus reducing the rate of the polymerization reaction which forms the fouling material. Applicant has discovered that the polymerization mechanism is dependent upon the presence of a second liquid, namely, an aqueous phase in the heads column. This aqueous phase provides the conditions conducive for the ionic polymerization of HCN, to form solid polymeric HCN. The polymeric HCN precipitates to block the active areas as well as downcomers of the distillation trays, and coheres to other polymeric HCN to foul the tower internals. Applicant's discovery of this previously unknown and unsuspected mechanism permits applicant to operate such distillation columns with significantly lower rates of HCN polymerization and resulting fouling. The enhanced operation can be effected by operating the heads column in a manner to reduce or eliminate the formation of this aqueous phase.

Since the formation of an aqueous layer was not appreciated as a potential source of HCN polymerization, there was no incentive to reduce the formation of this aqueous layer available in the current art. Techniques to reduce the formation of the aqueous layer include, but are not limited to, increased reflux ratios; the use of a side decanter to split and remove the aqueous phase from the column; use of a cooler feed stream to increase the stripping effectiveness of the column; increased number of stripping trays; use of an intermediate condensor above the feed to supplement the overhead condenser; subcooling the reflux stream; increased reboiler and overhead condensor duty to increase reflux flow rates; control operating pressure to shift the equilibrium between the two liquid phases; and methods that would increase reboiler duty, and associated stripping effectiveness of the head column. Increasing the hydrogen cyanide reflux or concentration of hydrogen cyanide above the feed tray can also be achieved by operating the reactor section of the process to produce higher weight percentages of HCN in the reactor product, increasing the percentage of HCN in the heads column feed, which results in the reduction or elimination of the second liquid phase. Any increased tray efficiency also allows more stripping effectiveness and is helpful in eliminating undesirable aqueous second liquid phase.

Preferably, the ammoxidation reaction is performed in a fluid bed reactor although other types of reactors such as transport line reactors are envisioned. Fluid bed reactors, for the manufacture of acrylonitrile are well known in the prior art. For example, the reactor design set forth in U.S. Pat. No. 3,230,246, herein incorporated by reference, is suitable.

Conditions for the ammoxidation reaction to occur are also well known in the prior art as evidenced by U.S. Pat. Nos. 5,093,299; 4,863,891; 4,767,878 and 4,503,001; herein incorporated by reference. Typically, the ammoxidation process is performed by contacting propane, propylene or isobutylene in the presence of ammonia and oxygen with a fluid bed catalyst at an elevated temperature to produce the acrylonitrile or methacrylonitrile. Any source of oxygen may be employed. For economic reasons, however, it is preferred to use air. The typical molar ratio of the oxygen to olefin in the feed should range from 0.5:1 to 4:1, preferably from 1:1 to 3:1. The molar ratio of ammonia to olefin in the feed in the reaction may vary from between 0.5:1 to 5:1. There is really no upper limit for the ammonia-olefin ratio, but there is generally no reason to exceed a ratio of 5:1 for economic reasons.

The reaction is carried out at a temperature of between the ranges of about 260° to 600° C., but the preferred ranges being 310° to 500° C., especially preferred being 350° to 480° C. The contact time, although not critical, is generally in the range of 0.1 to 50 seconds, with preference being to a contact time of 1 to 15 seconds.

In addition to the catalyst of U.S. Pat. No. 3,642,930, other catalysts suitable for the practice of the present invention are set forth in U.S. Pat. No. 5,093,299, herein incorporated by reference.

The conditions under which the absorber column, recovery column and heads column are maintained range between 5 to 7 psig (80° F. to 110° F.), and 1 to 4.5 psig (155° F. to 170° F.), respectively.

EXAMPLES

ASPENPLUS® process simulations of the heads column were used to identify operating conditions which eliminated the presence of an aqueous phase on trays above the column feed location. A column feed column temperature was selected and a tray efficiency specified. The reflux ratio of the heads column was then adjusted for each case until no aqueous third phase formed on trays above the column feed location. Acceptable product purity was defined as an overhead stream composition of less than 50 ppm acrylonitrile, and a bottoms stream composition of less than 100 ppm HCN.

For all examples, the heads column feed had a nominal composition of 83 wt % acrylonitrile, 10 wt % HCN and 7 wt % water, and was introduced to the heads column at a rate of 40,000 lb/hr at 30 psia. The heads column had 64 trays, a reboiler and an overhead condenser. The tray efficiency used in these simulations was 60%. For all examples, the trays are numbered starting from the Heads column top tray.

Example 1

The main feed was introduced to the column at tray 25. With a 100 degree feed temperature, the third aqueous phase was eliminated at the reflux ratio of 4.95, while still maintaining the overhead and bottoms products within specification limits. All reflux ratios below 4.95 formed an undesirable aqueous layer.

Example 2

The main feed location was moved up by five trays and the feed was introduced to the column at tray 20. With a 100 degrees F. feed temperature, the third aqueous phase was eliminated at the reflux ratio of 4.3, while still maintaining the overhead and bottoms products within specification limits. Thus, introducing 5 more stripping trays reduced the reflux required for the elimination of the undesirable aqueous phase from 4.95 in Example 1 to 4.3 in this case.

Example 3

The main feed at 80 degrees F. was introduced to the column at tray 25. With this colder feed temperature, the third aqueous phase was eliminated at the reflux ratio of 4.24 instead of 4.95 reported in Example 1, while still maintaining the overhead and bottoms products within specification limits.

Example 4

The primary feed was split in two portions: 75% of the feed was introduced on tray 20, and 25% of the feed was introduced on tray 25. The feed temperature was maintained at 100 degrees F. for both the portions. The third aqueous phase was eliminated at a reflux ratio of 4.1, while still maintaining the overhead and bottoms products within specification limits. This compares favorably with a reflux ratio required of 4.95 in Example 1 or 4.3 in Example 2.

Example 5

The primary feed was maintained at 100 degrees F. and was introduced on stage 25. An intermediate tray condenser withdrew all the liquid phase material from tray 20, cooled the material to 60 degrees F., and returned the cooled liquid material to tray 21. The third aqueous phase was eliminated at a reflux ratio of 4.6, while still maintaining the overhead and bottoms products within specification limits.

Example 6

The primary feed was maintained at 100 degrees F. and was introduced on tray 25. A total of 400 lb/hr of 99.8 wt % HCN, maintained at 80 degrees F., was fed to tray 20. The third aqueous phase was eliminated at the reflux ratio of 4.3, while still maintaining the overhead and bottoms products within specification limits. One should note here that the pure HCN addition can be made anywhere in the section between the Heads column top tray and the feed tray. Operation of an industrial facility with reactor conversion tuned to produce higher percentages of HCN in the reactor product stream, resulting in a higher percentage of HCN in the heads column feed streams would have results similar to this example.

Example 7

The primary feed was maintained at 100 degrees F. and was introduced on tray 25. A two-phase, side-decanter, which may be operated at sub-ambient temperatures, withdrew all the liquid phase material from tray 24, decanted the aqueous phase from the organic phase, and returned the organic phase material to tray 25. The third aqueous phase was eliminated at a reflux ratio of 4.8, while still maintaining the overhead and bottoms products within specification limits.

It should be further noted that combinations of various ideas to substantially or completely eliminate the formation of the undesirable aqueous phase can yield an optimum solution which would be determined by specific constraints. As will be evident to those skilled in the art, various modifications of this invention can be made or followed in light of the foregoing disclosure and discussion without departing from the spirit and scope of the disclosure or from the scope of the claims.

What is claimed is:

1. A process for the recovery of acrylonitrile, methacrylonitrile or hydrogen cyanide obtained from the reactor effluent of an ammoxidation reaction of propane, propylene or isobutylene comprising passing said reactor effluent through an absorber column, a recovery column and a heads column compsising a feed tray wherein the improvement comprises operating said heads column in a manner which inhibits the formation of an aqueous phase above the feed tray of said heads column wherein said manner is selected from one or more of the group consisting of:

(a) increasing the reflux ratio of said heads column to the point that no aqueous phase forms above the feed tray;

(b) using a side decanter to remove aqueous material from said heads column;

(c) wherein said heads column comprises stripping trays, increasing the number of stripping trays of said heads column;

(d) wherein said heads column comprises a reboiler with a reboiler duty, increasing the reboiler duty of said heads column;

(e) wherein said heads column comprises a reflux condenser, using an intermediate condenser above the feed tray of said heads column and below the reflux condenser of said heads column;

(f) wherein a feed stream enters the heads column, cooling the feed stream to a temperature that no aqueous phase forms above the feed tray;

(g) wherein said heads column comprises a reflux condenser and a reflux stream subcooling the reflux stream to said heads column; and (h) reducing operating pressure of said heads column so that the aqueous liquid phase is reduced with pressure reduction.

2. The process of claim 1 wherein the manner of operating the heads column which in inhibits the formation of an aqueous phase above the feed tray comprises increasing the reflux ratio of said heads column to the point that no aqueous phase forms above the feed tray.

3. The process of claim 1 wherein the manner of operating the heads column which in inhibits the formation of an aqueous phase above the feed tray comprises using side decanter to remove aqueous material from said heads column.

4. The process of claim 1 wherein the heads column comprises stripping trays and the manner of operating the heads column which inhibits the formation of an aqueous phase above the feed tray comprises increasing the number of striping trays of said heads column.

5. The process of claim 1 wherein the heads column comprises a reboiler with a reboiler duty, and the manner of operating the heads column which inhibits the formation of an aqueous phase above the feed tray comprises increasing the reboiler duty of said heads column.

6. The process of claim 1 wherein the heads column comprises a reflux condenser, and the manner of operating the heads column which inhibits the formation of an aqueous phase above the feed tray comprises using an intermediate condenser above the feed tray of said heads column and below the reflux condenser of said heads column.

7. The process of claim 1 wherein a feed stream enters the heads column, and the manner of operating the heads column which inhibits the formation of an aqueous phase above the feed tray comprises cooling the feed stream to a temperature that no aqueous phase forms above the feed tray.

8. The process of claim 1 wherein the heads column comprises a reflux condenser and a reflux stream, and the manner of operating the heads column which inhibits the formation of an aqueous phase above the feed tray comprises subcooling the reflux stream to said heads column.

9. The process of claim 1 wherein the manner of operating the heads column which inhibits the formation of an aqueous phase above the feed tray comprises reducing operating pressure of said heads column so that the aqueous liquid phase is reduced with pressure.

* * * * *

UNITED STATES PATENT AND TRADEMARK OFFICE
CERTIFICATE OF CORRECTION

| | | |
|---|---|---|
| PATENT NO. | : 6,793,776 B2 | Page 1 of 1 |
| APPLICATION NO. | : 09/945228 | |
| DATED | : September 21, 2004 | |
| INVENTOR(S) | : Sanjay P. Godbole | |

It is certified that error appears in the above-identified patent and that said Letters Patent is hereby corrected as shown below:

In column 2, line 66, replace "remove as an" with --removed--.

In column 6, line 57, replace "compsising" with --comprising--.

In column 7, line 23, after "stream" insert --,--.

In column 7, line 29, delete "in hibits" and insert therefore --inhibits--.

In column 7, line 34, delete "in hibits" and insert therefore --inhibits--.

Signed and Sealed this

Twenty-seventh Day of February, 2007

JON W. DUDAS
*Director of the United States Patent and Trademark Office*